(12) United States Patent
Hendriks et al.

(10) Patent No.: US 10,046,131 B2
(45) Date of Patent: Aug. 14, 2018

(54) PATIENT INTERFACE WITH CUSHION FOR RED MARK PREVENTION

(71) Applicant: KONINKLIJKE PHILIPS N.V., Eindhoven (NL)

(72) Inventors: Cornelis Petrus Hendriks, Eindhoven (NL); Susanne Maaike Valster, Valkenswaard (NL); Marc Matysek, Hofheim (DE); Sander Theodoor Pastoor, Utrecht (NL); Roland Alexander Van De Molengraaf, Geldrop (NL); Nicolaas Petrus Willard, Valkenswaard (NL); Richard Johannus Maria Van De Ven, Moergestel (NL); Joyce Van Zanten, Waalre (NL); Willem Potze, Geldrop (NL); Sima Asvadi, Eindhoven (NL); Rudolf Maria Jozef Voncken, Eindhoven (NL); Jacob Roger Haartsen, Eindhoven (NL); Mareike Klee, Straelen (DE); Matthew John Lawrenson, Bussigny-Pres-de-Lausanne (CH); Julian Charles Nolan, Pully (CH)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 226 days.

(21) Appl. No.: 14/405,063

(22) PCT Filed: Jun. 6, 2013

(86) PCT No.: PCT/IB2013/054648
§ 371 (c)(1),
(2) Date: Dec. 2, 2014

(87) PCT Pub. No.: WO2013/183018
PCT Pub. Date: Dec. 12, 2013

(65) Prior Publication Data
US 2015/0209540 A1    Jul. 30, 2015

Related U.S. Application Data

(60) Provisional application No. 61/657,150, filed on Jun. 8, 2012.

(51) Int. Cl.
*A61M 16/00* (2006.01)
*A61M 16/06* (2006.01)

(52) U.S. Cl.
CPC .... *A61M 16/0622* (2014.02); *A61M 16/0003* (2014.02); *A61M 16/0605* (2014.02);
(Continued)

(58) Field of Classification Search
CPC .......... A61M 16/0622; A61M 16/0683; A61M 16/0003; A61M 16/0605;
(Continued)

(56) References Cited

U.S. PATENT DOCUMENTS 5,355,878 A    10/1994   Griffiths
6,397,847 B1 *  6/2002   Scarberry ............. A61M 16/06
                                                           128/206.14
(Continued)

FOREIGN PATENT DOCUMENTS

CN    101528296 A    9/2009
CN    101574553 A    11/2009
(Continued)

*Primary Examiner* — Steven Douglas
(74) *Attorney, Agent, or Firm* — Michael W. Haas (57) ABSTRACT

A patient interface and a patient interface system comprise a responsive material and a method for preventing the formation of red marks due to wearing a patient interface that is pressing against the skin of a patient for a longer time and/or for reducing air leakages of the patient interface that may result from an unintended shift of the patient interface (Continued)

on the patient's face. The responsive material is configured for alternating the pressure exerted by the cushion element on the patient and/or the area on the patient where the pressure is exerted by the cushion element in response to a physical quantity acting on the responsive material. The formation of red marks and of air leakages can be reduced or even avoided by means of the responsive material.

8 Claims, 6 Drawing Sheets

(52) U.S. Cl.
CPC ..... *A61M 16/0683* (2013.01); *A61M 16/0633* (2014.02); *A61M 2016/0661* (2013.01); *A61M 2205/0266* (2013.01); *A61M 2205/0283* (2013.01); *A61M 2205/15* (2013.01); *A61M 2205/332* (2013.01); *A61M 2205/3368* (2013.01); *A61M 2230/06* (2013.01); *A61M 2230/30* (2013.01)

(58) Field of Classification Search
CPC ...... A61M 2205/3368; A61M 2205/15; A61M 2230/06; A61M 2230/30; A61M 16/0633; A61M 2205/0283; A61M 2205/332; A61M 2016/0661; A61M 2205/0266
See application file for complete search history.

(56) References Cited

U.S. PATENT DOCUMENTS

| | | | |
|---|---|---|---|
| 8,371,293 B2* | 2/2013 | Henry | A61H 9/0078 128/200.24 |
| 8,490,624 B2 | 7/2013 | Ho | |
| 8,522,784 B2* | 9/2013 | Ng | A61M 16/06 128/205.25 |
| 9,132,255 B2* | 9/2015 | Skipper | A61M 16/06 |
| 9,724,488 B2 | 8/2017 | Guney | |
| 2004/0008853 A1 | 1/2004 | Pelrine | |
| 2004/0163648 A1 | 8/2004 | Burton | |
| 2005/0076906 A1 | 4/2005 | Johnson | |
| 2005/0199239 A1* | 9/2005 | Lang | A61M 16/06 128/206.24 |
| 2006/0144399 A1* | 7/2006 | Davidowski | A61M 16/06 128/205.12 |
| 2007/0095349 A1 | 5/2007 | Hansmann | |
| 2008/0289633 A1 | 11/2008 | Kwok | |
| 2008/0314390 A1 | 12/2008 | Kwok | |
| 2009/0078273 A1 | 3/2009 | Bhat | |
| 2011/0146689 A1 | 6/2011 | Curley | |
| 2011/0220110 A1 | 9/2011 | Frater | |
| 2012/0080035 A1 | 4/2012 | Guney | |
| 2012/0103339 A1 | 5/2012 | Koehler | |
| 2014/0109911 A1* | 4/2014 | Asvadi | A61M 16/06 128/205.25 |
| 2014/0123981 A1* | 5/2014 | Willard | A61M 16/06 128/205.25 |
| 2014/0251338 A1* | 9/2014 | Asvadi | A61M 16/06 128/206.22 |

FOREIGN PATENT DOCUMENTS

| | | |
|---|---|---|
| CN | 201888979 U | 7/2011 |
| EP | 1902743 B1 | 2/2011 |
| JP | 2005537906 A | 12/2005 |
| JP | 2010508998 A | 3/2010 |
| RU | 2392010 C1 | 6/2010 |
| WO | WO9200120 A1 | 1/1992 |
| WO | WO2004075953 A1 | 9/2004 |
| WO | WO2008053666 A1 | 5/2008 |
| WO | WO2013067582 A1 | 5/2013 |

* cited by examiner

PATIENT INTERFACE WITH CUSHION FOR RED MARK PREVENTION

CROSS-REFERENCE TO RELATED APPLICATIONS

This patent application claims the priority benefit under 35 U.S.C. § 371 of international patent application no. PCT/IB2013/054648, filed Jun. 6, 2013, which claims the priority benefit under 35 U.S.C. § 119(e) of U.S. Provisional Application No. 61/657,150 filed on Jun. 8, 2012, the contents of which are herein incorporated by reference.

FIELD OF THE INVENTION

The present invention relates to a patient interface with a cushion element and an electroactive polymer material, a method for preventing the formation of red marks by a patient interface and/or for reducing gas leakages of the patient interface and a cushion element for use in a patient interface.

BACKGROUND OF THE INVENTION

Patient interfaces, such as masks for covering the mouth and/or nose, are used for delivering gas to a patient. Such gases, like air, cleaned air, oxygen, or any modification of the latter, are submitted to the patient via the patient interface in a pressurized or unpressurized way.

For several chronic disorders and diseases, a long-term attachment of such a patient interface to a patient is necessary or at least advisable.

One non-limiting example for such a disease is obstructive sleep apnoea or obstructive sleep apnoea syndrome (OSA). OSA is usually caused by an obstruction of the upper airway. It is characterized by repetitive pauses in breathing during sleep and is usually associated with a reduction in blood oxygen saturation. These pauses in breathing, called apnoeas, typically last 20 to 40 seconds. The obstruction of the upper airway is usually caused by reduced muscle tonus of the body that occurs during sleep. The human airway is composed of walls of soft tissue which can collapse and thereby obstruct breathing during sleep. Tongue tissue moves towards the back of the throat during sleep and thereby blocks the air passages. OSA is therefore commonly accompanied with snoring.

Different invasive and non-invasive treatments for OSA are known. One of the most powerful non-invasive treatments is the usage of Continuous Positive Airway Pressure (CPAP) or Bi-Positive Airway Pressure (BiPAP) in which a patient interface, e.g. a face mask, is attached to a tube and a machine that blows pressurized gas, preferably air, into the patient interface and through the airway in order to keep it open. Positive air pressure is thus provided to a patient through a hose connected to a patient interface or respiratory interface, such as a face mask, that is worn by the patient. The afore-mentioned long-term use of the patient interface is the result, since the wearing of the patient interface takes place during the sleeping time of the patient.

Examples for patient interfaces are:
nasal masks, which fit over the nose and deliver gas through the nasal passages,
oral masks, which fit over the mouth and deliver gas through the mouth,
full face masks, which fit over both, the nose and the mouth, and deliver gas to both, and
nasal pillows, which are regarded as masks as well within the scope of the present invention and which consist of small nasal inserts that deliver the gas directly to the nasal passages.

The patient interface is usually positioned on the patient's head using some kind of headgear. Wearing a patient interface can be uncomfortable, since for providing an airtight seal between the patient interface and the patient's face, the patient interface has to be worn tightly on the face. Further, the patient interface may comprise a forehead support. Such a forehead support is often designed as a pad that touches the forehead of a patient during use. It is often included in order to relief the pressure of the patient interface on the nose bridge.

In order to remedy that the wearing of the patient interface is uncomfortable, US 2008/0314390 A1 suggests to equip a facial mask with an automatically adjusting forehead support. This forehead support is adapted to be movable between two positions and includes a biasing mechanism that urges the forehead support in the second position. Thereby a more comfortable wearing of the mask shall be achieved.

However, as a part of such a patient interface being uncomfortable, the tightly wearing of the patient interface on the face may result also in pressure points and red marks once the patient interface is removed.

In another aspect, even if the patient interface is tightly mounted on the patient's face initially, the patient interface may start leaking during the sleeping time, thereby reducing the effectiveness of the medical treatment. When a patient turns to his side, the pillow may shift the patient interface relatively to the face. This can result in leakage of the patient interface. Another cause for leakage may be the relaxation of facial muscles as soon as the patient falls asleep. As a consequence, the stiffness of the facial surface changes and induces leakage of the patient interface. Therefore, there is a need for an automatic re-adjustment of the patient interface due to a shifted position of the interface and a muscle relaxation during the sleeping time of the patient.

In a further aspect, each patient's face features an individual facial contour. As an example, the size of the nose can vary from face to face. If the patient interface is only offered in one standard size, the large-nosed patients feel more seal pressure and less comfort, since the large nose stretches the seal more than a smaller nose. As a remedy, it is known to manufacture custom patient interfaces. However, this requires expensive and time consuming calibration work.

SUMMARY OF THE INVENTION

It is an object of the present invention to provide a device and a method which provide a reduction of the formation of red marks, preferably avoiding them completely, which therefore improve the comfort for a patient wearing a patient interface and/or which reduce leakage during the usage of the patient interface.

According to an aspect of the present invention, a patient interface for delivering gas to a patient is provided, with
a cushion element that gets in contact with the patient when the patient interface is worn by the patient, and
a responsive material for alternating the pressure exerted by the cushion element on the patient and/or the area on the patient where the pressure is exerted by the cushion element in response to a physical quantity acting on the responsive material, wherein the cushion element comprises or is mounted to the responsive material.

The term "cushion element" as used within the context of the present invention is to be understood as a part of the patient interface normally comprising a soft material and being arranged on the side of the patient interface that is directed to and is getting in contact with the patient when the patient interface is worn by the patient. Thereby this cushion element provides an airtight seal and/or makes the wearing of the patient interface more comfortable for the patient. Therefore, the cushion element may be a part of the mask part which provides the gas to the patient or any other part of the patient interface that gets in contact with the patient, like a forehead support, a headgear etc. Accordingly, other words for describing this "cushion element" would be cushion, seal, pad, or the like.

The term "alternating" as used within the context of the present invention is to be understood as swapping/switching between different values of the pressure in any desired time pattern as well as changing/modifying the pressure to a different value for an indefinite time.

In a preferred embodiment the responsive material is an electroactive polymer material, a temperature-responsive polymer material or a light-responsive polymer material. Thus, the physical quantity is preferably an electrical current or voltage, temperature or light. By use of the respective physical quantity the responsive material can be influenced in a controlled manner.

The term "electroactive polymer material" as used within the context of the present invention is to be understood as a polymer material that is able to change its properties, preferably its shape, more preferably its thickness and/or length due to the application of an electric field.

The term "temperature-responsive polymer material" as used within the context of the present invention is to be understood as a polymer material that is able to change its properties, preferably its volume dependent on the temperature. Most preferably this term refers to polyacrylates PNIPA (Poly(N-isopropylacrylamide)) that change their volume at a temperature near that of the human body (e.g. around 30-35° C.). When heated, for example, above 32° C., PNIPA undergoes a reversible lower critical solution temperature phase transition from a swollen hydrated state to a shrunken dehydrated state, losing a part of its volume. The temperature-responsive polymer material may also refer to a SMM (shape memory material) that is able to change its mechanical properties (going from rigid to flexible for example) as a response to a temperature change. Further, the SMM can be a 1-way or 2-way shape memory material. If the SMM is a 2-way shape memory material, the pressure exerted by the cushion element on the patient can be varied in an arbitrary timely pattern by means of a temperature regulation affecting the SMM.

According to another aspect of the present invention, a method for preventing the formation of red marks by a patient interface on a skin of a patient and/or for reducing gas leakages of the patient interface is provided, with the following steps:

attaching a patient interface to a patient via a cushion element on the patient interface such that the cushion element contacts the skin of the patient, and alternating the pressure exerted by the cushion element on the patient and/or the area on the patient where the pressure is exerted by the cushion element by a responsive material comprised in the cushion element in response to a physical quantity acting on the responsive material.

According to another aspect of the present invention, a cushion element for use in a patient interface is provided, comprising a responsive material for alternating the pressure exerted by the cushion element on the patient and/or the area on the patient where the pressure is exerted by the cushion element in response to a physical quantity acting on the responsive material Preferred embodiments of the invention are defined in the dependent claims.

Red marks are formed when too much pressure is applied to the skin and the blood vessels, especially the arteries, in the pressed area are narrowed and/or closed for a prolonged time.

With the aid of the aforementioned electroactive polymer material it is possible to alternate the pressure, for example in a time-dependent manner, such that the constant prolonged pressure causing the formation of red marks is avoided. Further, it is also possible to alternate the pressure distribution over the patient interface. This will allow arteries in the skin of the patient that were compressed due to the pressure of the patient interface on the skin to reopen if the pressure is lowered.

Electroactive polymer materials, also known as electroactive polymers, are polymers that are able to change their size and/or shape by the application of an electric field. Accordingly, they can be designed in any suitable size and shape. Therefore, they can be included in the aforementioned cushion element of the patient interface quite easily. Electroactive polymer materials can also be manufactured as very thin and flexible materials and do not increase the weight of the patient interface in a significant way. In other words, they are very flexible, thin and lightweight. Due to the design of electroactive polymers, i.e. because of the absence of any mechanical elements like motors, valves or the like, these electroactive polymer materials are noiseless and do not require any maintenance. Further, due to the resulting force being normally the result of electrostatic forces the power consumption is quite low.

The aforementioned alternating pressure leads basically to alternating the shape of the cushion element. The result in the patient interface according to the present invention, or the method according to the present invention, is an alternating pressure exerted on the skin of the patient, which can also be regarded as a small massaging action. This further improves the blood flow in the arteries within the skin of the patient.

In another aspect of the present invention, the aforementioned responsive material is also suitable for re-adjusting the cushion element to a patient's face when the patient interface, for example, has been shifted during the sleeping time relatively to its initial fitting position. The shift of the patient interface may be caused by a pillow pushing against the interface due to a change of the sleeping position or by a relaxation of the facial muscles of the patient falling asleep. This displacement usually leads to a leakage of the patient interface, thereby leading to a reduction of the effectiveness of the medical treatment as well as to a leaking air flow which may cause eye irritations and annoying noises of flow. By applying an electric field to the electroactive polymer material, the cushion element can be re-adjusted to the patient's face. Leakages can be reduced or even avoided. Similarly, if the temperature-responsive polymer material is used as the responsive material, leakages lead to a lowered temperature in the respective region of the cushion element and thus cause a volume change of the temperature-responsive polymer material. By means of this volume change, the leakages can be closed.

In a further aspect of the present invention, the electroactive polymer material can also be used to fit the patient interface to an individual facial geometry. In response to an applied electrical voltage the electroactive polymer material can stretch in an area dimension and contract in a thickness dimension of the polymer material, thereby allowing fitting the patient interface, for example, to different sizes of a nose. Therefore nose-size dependent pressure on the patient's face can be avoided.

According to another embodiment of the patient interface, the responsive material is segmented. Since electroactive polymer materials can be designed in several segments, each segment being able to be controlled separately, any desired motion pattern can be used for the electroactive polymer materials included in the cushion element of the patient interface according to the present invention. Accordingly, it would be possible to increase the pressure of the patient interface in the nose region of the patient, wherein the pressure in the region of the cheeks of the patient is lowered at the same time, for example. This may be inverted after a predetermined time, or be changed according to any other pattern where the pressure distribution on the skin of the patient is alternated in a time-dependent manner, for example.

The various segments can also be used to seal the patient interface in a region of a leakage that occurred, for example, after a change of a sleeping position of the patient. This may be done by applying different voltages to the segments made of the electroactive polymer material, wherein the voltages are chosen such that the effected deformation of the electroactive polymer material leads to a sealing of the patient interface. In case the segments are made of the temperature-responsive material, the leakages induce a temperature change, which, in turn, causes a modification of the volume of the temperature-responsive material and thus a closing of the leakages. Further, the segments can be utilized for adapting the patient interface, for example, to exposed regions of the patient's face, like the nose, chin etc. For an effective adaption, the segments may be particularly arranged at these exposed regions. By applying an electric field to the electroactive polymer material, the patient interface is adapted to the individual facial geometry, thereby leading a good sealing quality and wearing comfort.

According to another embodiment of the patient interface, the patient interface comprises at least one dielectric elastomer actuator as an electroactive polymer material. Dielectric elastomer actuators (DEA) are a preferred kind of electroactive polymer materials. This is due to this DEAs being able to produce large strains (up to 300%). Since they comprise a simple working principle DEAs can transform electric energy directly into mechanical work. Also, they are able to work in the opposite direction, i.e. transforming mechanical work into electric energy. They are basically designed as an electroactive polymer as dielectric sandwiched between two electrodes. Depending on the electrode voltage the thickness of the electroactive polymer may be changed. Accordingly, the thickness change results in a change in elongation. The result in the usage of such a DEA for a patient interface according to the present invention is that based on the change in thickness the pressure can be alternated and at the same time, due to the change in elongation, the skin may get stretched. Based on the aforementioned effect that a change in thickness by an external pressure results in a measurable electric energy at the electrodes, such a DEA may be used to detect pressure peaks or other selective pressure values. Especially DEAs, but also electroactive polymer materials in general, can be submitted to a voltage with a certain frequency resulting in a permanent changing of the shape of the electroactive polymer material. This basically represents one example of the aforementioned massaging action. Further, DEAs can be easily applied for the applications of the present invention.

The aforementioned effect that the DEA is able to transform mechanical work into electric energy can also be used to detect air leaks between the patient interface and the patient's face. In particular, the deformation of the electroactive polymer material can be monitored by measuring the material's electrical capacitance. Dependent on the determined deformation, an electrical voltage is applied to the electroactive polymer material in order to bend the material and to close the air leaks. Moreover, the effect of transforming a deformation of the electroactive polymer material in an electrical voltage can be used to detect excessive pressures between the patient interface and e.g. exposed regions of the patient's face, like the nose bridge. If such excessive pressures are detected, an electric field is applied to the respective DEA to reduce the pressure to a comfortable value.

According to another embodiment of the patient interface, at least one of the dielectric elastomer actuators is prestrained. This measure has the effect that such a prestrained, or prestretched, DEA shows a higher electrical breakdown strength. This means that a higher electrical field may be applied. Further, the relative pressure due to the actuation can be much higher compared to unstrained polymers when using the same voltage. Alternatively, in order to achieve the same pressure a lower voltage may be applied. This increases the safety of the material and reduces the power consumption. Also, a prestrain may be used for achieving a preferred actuation in a specific direction. Especially in in-plane movements, i.e. elongation, they show a much better actuator performance. This may be used either in a stretching application and/or in an antagonistic setup. In the latter, a material that is connected to the prestrained DEA is temporarily deformed upon actuation of the DEA and returns back to its previous shape after the actuation by the DEA. For the purposes mentioned before, the prestrained DEA(s) might be used as a single actuator in the patient interface according to the present invention, or together with regular DEAs, or electroactive polymer materials in general.

According to another embodiment of the patient interface, the cushion element comprises a plurality of temperature sensors. The temperature sensors can be realized, for example, as an array of small temperature dependent resistors that are distributed over the cushion element. By means of the temperature dependent resistors a temperature distribution of the cushion element can be determined. The temperature distribution, in turn, provides an indication for potential leakages of the cushion element. As soon as a leakage is detected corresponding counter measures can be triggered (for example by applying a voltage to the respective DEA).

In an embodiment the patient interface further comprises a shell, wherein the cushion element is mounted to the shell by the responsive material, in particular by electroactive polymer material. By changing the physical quantity acting on the responsive material, e.g. the electric field applied to the electroactive polymer material, the area where the cushion element contacts the skin of the patient can be changed. For instance, by modulating the physical quantity acting on the responsive material over the course of the night the amount of contact of the cushion element to any area of the skin can be reduced allowing moisture to dry from areas previously in contact with the cushion.

Preferably, the patient interface further comprises a support material arranged between the cushion element and the shell in parallel to the responsive material. The support material may be a stiff material that can provide a mechanical support, but can be compressed by the responsive material when the responsive material is acted on by a physical quantity to change its size and/or shape. Thus, the preciseness of the movement of the cushion element and the support of the cushion element (i.e. the fixation to the shell) can be further increased.

In still another embodiment of the patient interface said cushion element is ring-shaped and said responsive material is formed as ring arranged at the inner circumference of said cushion element. This provides another option for effecting a movement of the cushion element to change the area where the cushion element contacts the skin.

According to another aspect of the present invention a patient interface system is provided, with a patient interface of any of the aforementioned embodiments, preferably further comprising a controller for controlling the electroactive polymer material. The controller has the effect that it may be designed or programmed to control the electroactive polymer materials by any desired pattern via which the pressure of the patient interface against the skin of the patient is alternated via the electroactive polymer materials. This pattern may be a general pattern used for all patients, a random pattern, or a pattern designed especially for an individual patient. Accordingly, the controller is preferably designed to alternate the shape of the electroactive polymer material.

The controller can also be programmed such that the sealing quality of the patient interface is substantially maintained even if the patient interface got out of place e.g. while the patient is sleeping. In this embodiment, the controller causes the DEA(s) to bend in such a manner that the detected air leaks can be closed. Further, the controller can also be configured to adapt the patient interface to the individual facial geometry of the patient. Thereby, the patient interface can be customized without any time consuming calibration work.

According to another embodiment of the patient interface system, the patient interface comprises the controller. Such a design results in a patient interface system that is compact and works without any additional wiring or other connections in order to connect an external controller to the electroactive polymer materials over a longer distance.

According to another embodiment of the patient interface system, the patient interface system further comprises a device for supplying gas to the patient interface, wherein the device for supplying gas comprises the controller. This design has the effect that the patient interface itself is as lightweight as possible. All controlling parts, belonging either to the supply of gas or also to the electroactive polymer materials, are included in an external device.

According to another embodiment of the patient interface system, the controller is designed to receive pressure readings from the electroactive polymer material, and is preferably designed to alternate the shape of the electroactive polymer material based on these pressure readings. This measure has the effect that the controller is able to detect where pressure peaks on the skin of the patient appear as a result of wearing the patient interface. Based on these data regarding the pressure peaks and the pressure distribution the controller is then able to modify this pressure distribution. This is done by controlling the electroactive polymer materials, i.e. their shape.

Additionally, the pressure readings can be evaluated to determine the existence and the position of air leaks (one exemplary criterion is a skin contact pressure near zero) and to correspondingly control the electroactive polymer material to reduce or even avoid the leakage. Furthermore, the pressure readings hint at maladjustments of the patient interface to the patient's face. So, detected pressure peaks can be reduced by applying a respective electric field to the electroactive polymer material in order to enhance the wearing comfort.

According to another embodiment of the patient interface system, the controller is coupled to the plurality of temperature sensors. This embodiment allows the detection of leakages based on the temperature distribution of the cushion element as any leakage will cool the skin and the cushion element. If the cushion element has a uniform temperature or the temperature distribution is stable then the cushion element is considered without leakage. Any change in the temperature is in an indication for a leakage. When a potential leak of gas is detected, the controller may apply a corresponding voltage to the respective DEA(s) in order to close the leak.

According to another embodiment of the method according to the present invention, alternating the shape of the cushion element is based on the detected localized pressures of the patient interface on the skin.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
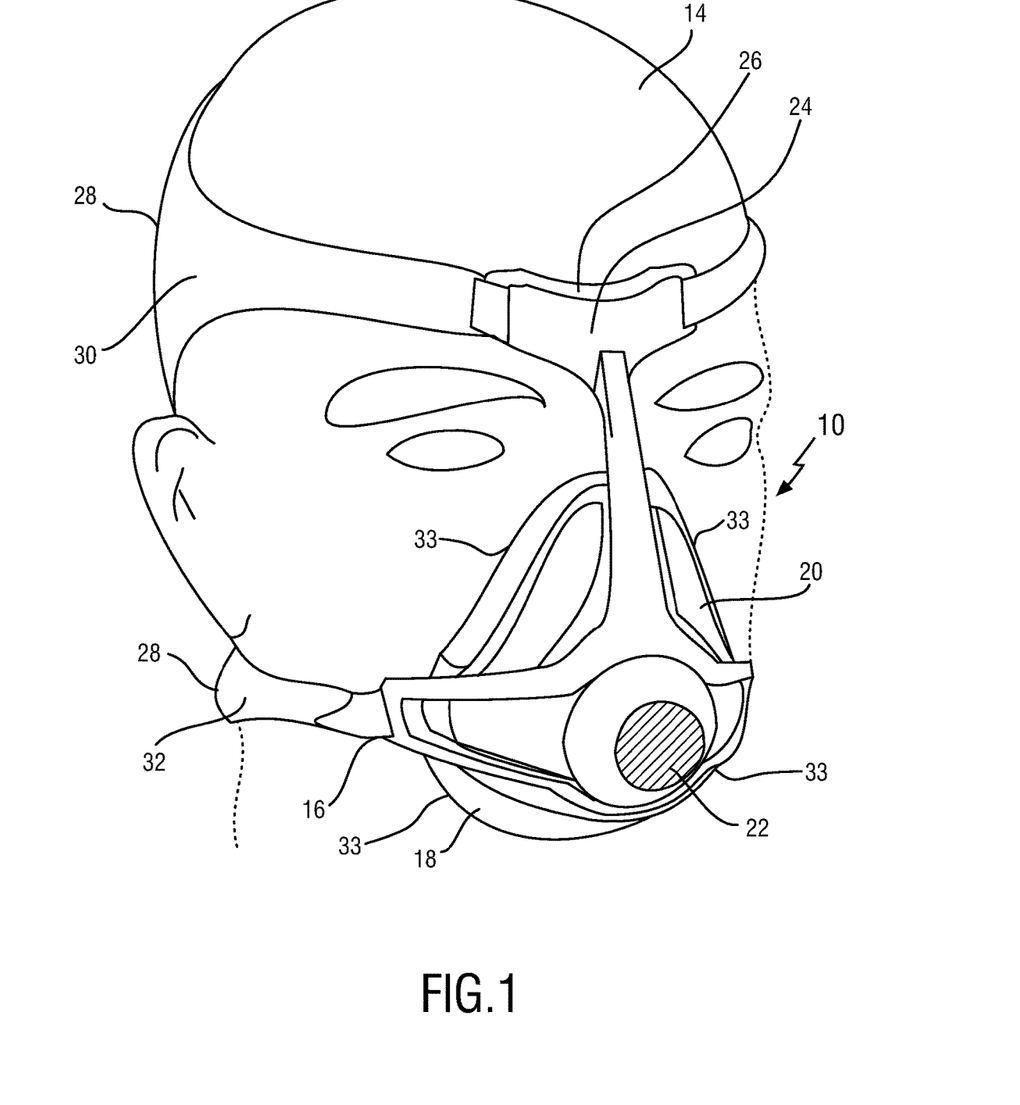
FIG. 1 shows a schematic perspective view of a patient wearing a patient interface according to the present invention.
Figure 2A:
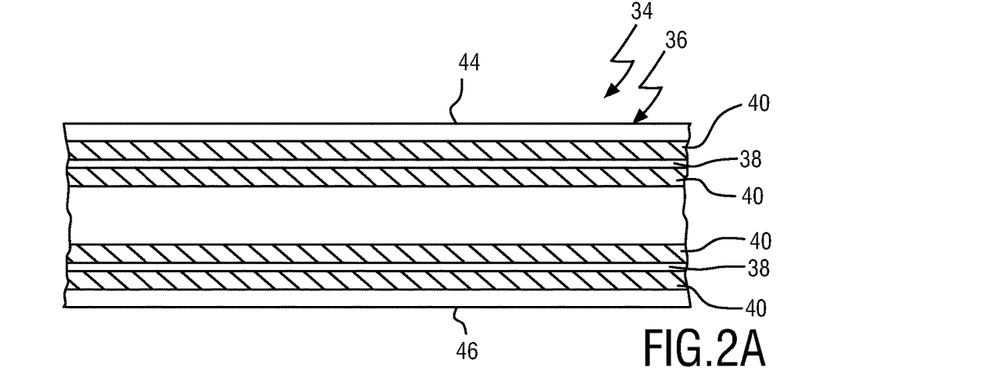
FIG. 2 shows a cross section of an electroactive polymer material.
Figure 2B:
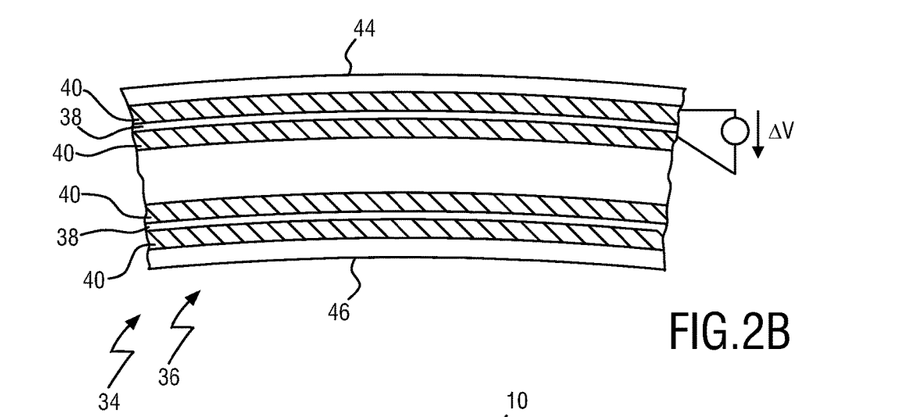
Figure 3:
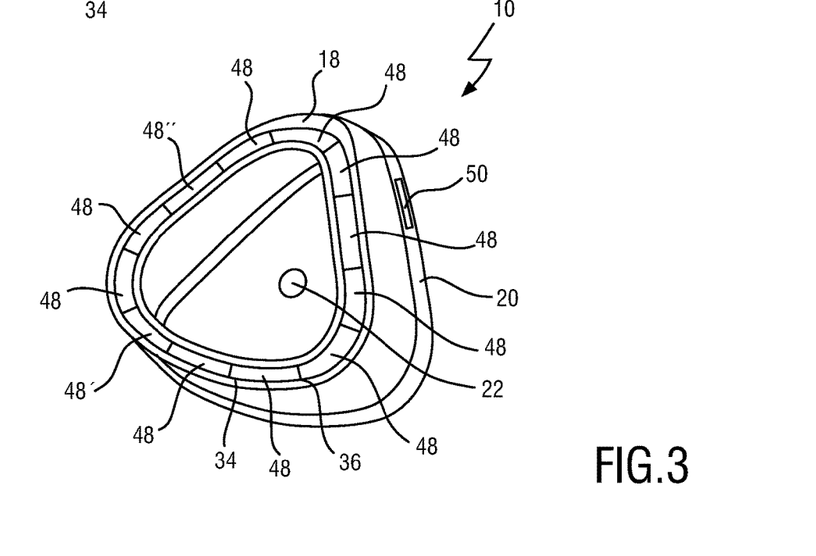
FIG. 3 shows a schematic perspective view of the patient interface with the electroactive polymer material according to the present invention.
Figure 5:
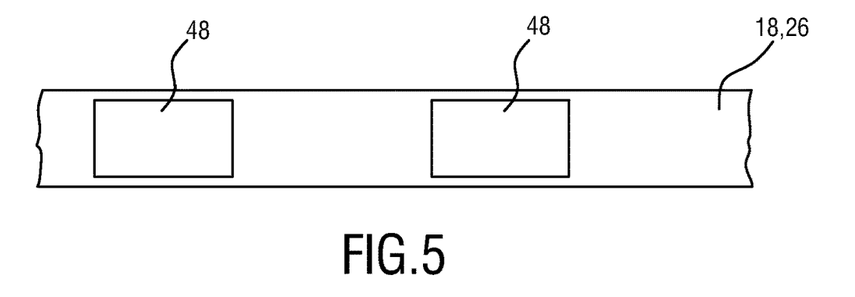
FIG. 5 shows a section of the patient interface comprising the electroactive polymer material according to another embodiment of the present invention.
Figure 6:
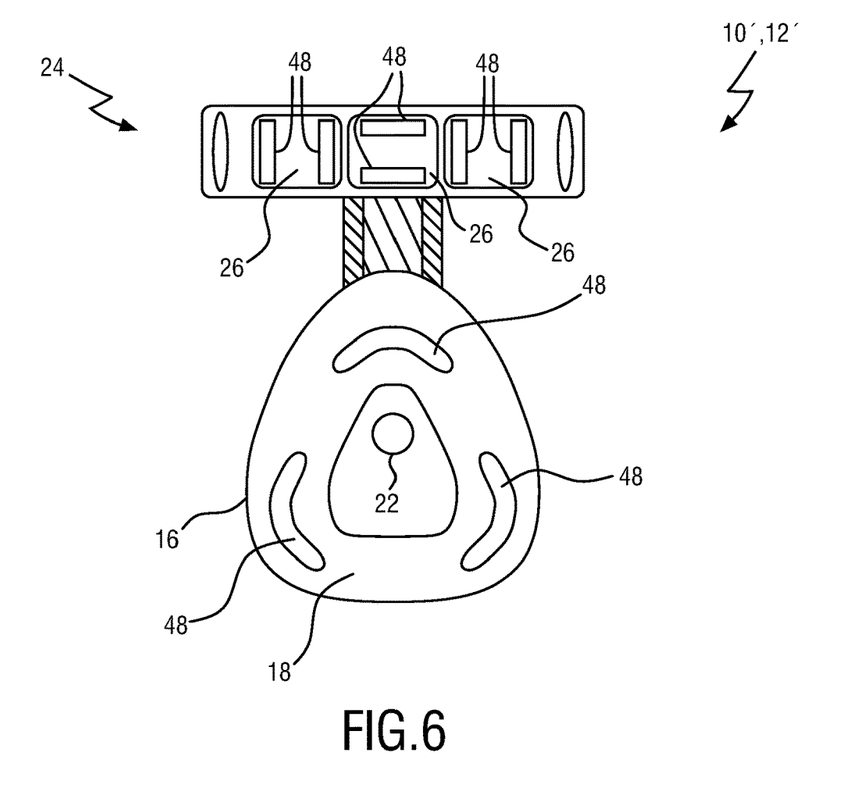
FIG. 6 shows a schematic perspective view of the patient interface with the electroactive polymer material according to another embodiment of the present invention.
Figure 7:
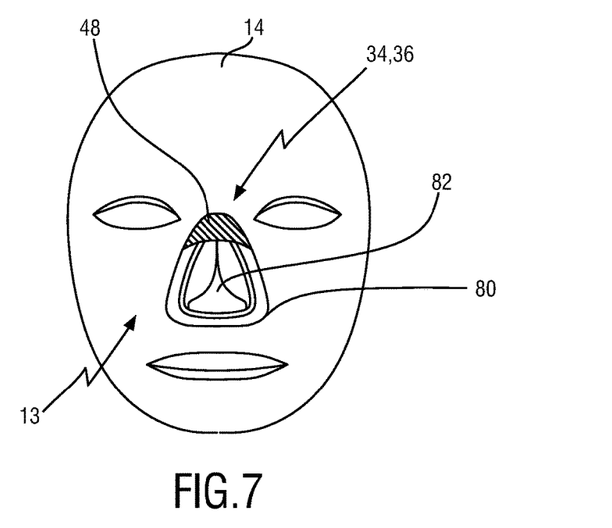
FIG. 7 shows a schematic perspective view of the patient wearing the patient interface according to another embodiment of the present invention.

An embodiment of a patient interface according to the present invention is shown throughout and described with the help of FIGS. 1 to 3, and is designated in its entirety by the reference numeral 10. Another embodiment of a patient interface according to the present invention is shown in and described with the help of FIG. 4, and is designated in its entirety by the reference numeral 12. Further, a patient interface system according to the present invention comprising the patient interface 12 is shown in and described with the help of FIG. 4 and is designated in its entirety by the reference numeral 60. FIGS. 5 and 6 illustrate a further embodiment of the patient interface according to the present invention which is denominated by the reference numeral 10' and 12', respectively. A further embodiment of the patient interface shown in FIG. 7 is referenced by reference sign 13.

The patient interface 10, shown in FIG. 1, is worn by a patient 14. In this certain embodiment, the patient interface 10 comprises a full face mask 16 covering the mouth and nose of the patient 14. The full face mask 16 comprises a cushion element, in the form of a cushion 18, and a shell 20. The cushion 18 is arranged on the shell 20 on that side that is directed to the face of the patient 14 in order to make the wearing of the full face mask 16, and of the patient interface 10 in general, more comfortable and especially to provide an airtight seal of the full face mask 16 on the patient's face. For this, the cushion 18 is comprised of a soft material, like silicone rubber or any other rubber or suitable elastic material. On the opposite side directing away from the patient's face, the shell 20 comprises a connector 22. Via this connector 22 the patient interface 10 is able to be connected to a hose (not shown) via which the (pressurized) gas can be submitted to the patient 14. In order to reduce the pressure on the nose bridge of the patient 14 the patient interface 10 further comprises a forehead support 24. This forehead support 24 is directly connected to the shell 20 of the full face mask 16. Thereby, a more even distribution of the force exerted on the nose region of the patient 14 is achieved. For improving the comfort when the forehead support 24 is pressing against the skin of the patient 14, the forehead support 24 comprises a cushion 26 as a cushion element.

For attaching the full face mask 16 on the patient 14, the patient interface 10 further comprises a headgear 28. This headgear 28 is in this certain embodiment of FIG. 1 comprised of two straps 30 and 32 circumventing the head of the patient 14, thereby attaching the patient interface 10 with a certain attachment force on the patient's face.

Because of this attachment force, the patient interface 10, especially the cushion 18 presses against the skin of the patient 14 that lies under said cushion 18. This may result in the formation of red marks due to the stop of the blood flow in the arteries within the skin of the patient 14 in this area. Also, the cushion 26 of the forehead support 24 presses against the skin of the patient 14, which may also lead to the formation of red marks in that area.

In spite of high attachment forces, the patient interface 10 may shift from its initial fitting position on the face of the patient 14, due to a patient sleeping on his/her side and thereby provoking lateral forces pushing against the patient interface 10. This shifting may result in air leakages 33 impairing the medical treatment. The gap sizes of the air leakages 33 may vary, for example, from 1 mm to 5 mm.

In order to prevent the formation of red marks on the skin of patient 14 the patient interface 10 comprises an electroactive polymer material 34. This is shown in more detail in FIG. 2, for example.

FIG. 2 shows an exemplary cross section of the electroactive polymer material 34, which is designed as a dielectric elastomeric actuator (DEA) 36. As illustrated in FIG. 2A, the DEA 36 comprises an elastomeric film 38 which is sandwiched between electrodes 40, wherein the film 38 and the electrodes 40 are integrated in a cushion material 42 (made e.g. of silicone). The electrodes 40 may comprise carbon material. Further, the DEA 36 comprises a first protective layer 44 touching the skin of the patient 14 and isolating the electrodes 40 and a second protective layer 46 for isolating/protecting the electrodes 40. The protective layers 44, 46 may comprise silicone. The DEA 36 illustrated in FIG. 2A can have an overall thickness of about 400 μm. As a result, the integration of the DEA 36, for example, into the cushion 18 and/or 26 may be done with minimum space requirements. Additionally, the DEA 36 is very light-weight. When applying an electrical voltage V to the electrodes 40 (see FIG. 2B), the electrodes 40 move towards each other and cause a stretching of the elastomeric film 38. This stretching leads to a deformation of the electroactive polymer material 34 and can therefore be used to manipulate the fitting of the patient interface 10.

FIG. 3 shows the patient interface 10 without the headgear 28 and the forehead support 24 for clarity reasons. Arranged in the cushion 18 of the patient interface 10 is the electroactive polymer material 34. In this certain embodiment, the electroactive polymer material 34 is designed as the dielectric elastomeric actuator (DEA) 36. This embodiment of the DEA 36 comprises several sections 48. Aside from this special embodiment where a single DEA 36 comprises several sections 48, a design wherein the electroactive polymer material 34 comprises a plurality of single DEAs corresponding to the sections 48 lies also within the scope of the present invention.

This electroactive polymer material 34, i.e. the DEA 36, is arranged in a way in the cushion 18 that the electrodes 40 of the DEA (not shown in FIG. 3) are shielded from the skin of the patient 14. This can for example be realized by the DEA 36 being included within the cushion 18. In order to control the DEA 36, i.e. the sections 48, the patient interface 10 further comprises a controller 50. This controller 50 is schematically shown in FIG. 3 as being included within the shell 20. The controller 50 is separately connected to each section 48 of the DEA 36. Thereby, the controller 50 may control each section 48 individually.

The mode of application of the DEA 36, i.e. the electroactive polymer material 34, is preferably such that the controller 50 induces a change in the shape of the sections 48. This change in shape can be, for example, either an increase of the thickness of a section 48, thereby also increasing the pressure of the patient interface 10 on the skin of the patient 14, or a decrease of the thickness of a section 48, thereby also lowering the pressure of the patient interface 10 on the skin of the patient 14. This may be done in an alternating way, like, for example, increasing the thickness of the section 48' and simultaneously decreasing the thickness of the section 48" as a first step, and then decreasing the thickness of the section 48' while simultaneously the thickness of the section 48" is increased in a second step. This changes the pressure profile or the pressure distribution of the patient interface 10 pressing against the skin of the patient 14.

The delay between the first step and the second step in this example gives a frequency for the change in the pressure profile of the patient interface 10. This delay can either be relatively small, like one second or less, for example, or may also be relatively large in the area of several minutes, like 5 min. by way of example. The first example results in a vibration- or massage-like action, wherein the second example would be preferably used if merely a distribution of the force pressing against the patient's skin shall be achieved and a constant pressure shall be avoided. The example mentioned before was merely used by way of example and is not meant to limit the present invention. Accordingly, the mode of actuating the respective sections 48 may be different, e.g. by comprising simultaneous or non-simultaneous changes, a combination of actuations with, for example, different frequencies may be used and any number of sections 48 may be actuated in order to achieve a desired change, reaching from merely one to all sections 48.

Preferred embodiments might also comprise a certain number of actuation configurations, wherein each configuration has a predefined pattern which sections 48 (or DEAs, depending on the realization) are actuated and which sections 48 are not actuated. The controller 50 may then switch between these configurations. This may be possible in a predetermined or random manner. The number and the layout of the different configurations may vary and may depend on the number of sections 48 used for the electroactive polymer material 34, for example. Preferably, the number and the way of switching between the available configurations is chosen in a way such that the design is as efficient as possible, e.g. allows a re-use of the charges used to actuate the sections 48, requires as few wires as possible, and works with less active switches, i.e. comprises less complexity and is energy-efficient.

Since the sections 48 are included within the cushion 18, preferably in a form-fit way, the change of the shape of a section 48 induces also a change of the shape of the cushion 18 in the area where the respective section 48 is located. This can either be a thickening of the cushion 18 in that area by increasing the thickness of the respective section 48, or it may be a stretching of the area of the cushion 18 by decreasing the thickness of the respective section 48 which correspondingly leads to an elongation of the section 48. Provided there is a suitable friction between the cushion 18 and the skin of the patient 14, as it is the case for silicone rubber as a cushion material, for example, this stretching of the respective area of the cushion 18 leads to a stretching of the skin of the patient 14.

In one preferred embodiment, the DEA 36 is prestrained, at least in some sections 48. Thereby, the shape of the cushion 18 can either be changed between predefined states in an antagonistic fashion, or the elongation movement, i.e. in-plane movement, may be the primary actuation result such that the aforementioned stretching may be achieved in an effective way, if desired.

As mentioned before, the forehead support 24 may comprise a cushion 26. In order to reduce the formation of red marks by this forehead support 24 the cushion 26 may comprise DEAs as well. In accordance with the design of the DEA 36, the DEA (not shown) in the cushion 26 may be designed as one single DEA or may also comprise several DEAs. In the first case it is of course also possible that the DEA in the cushion 26 is separated in several sections.

Figure 4:
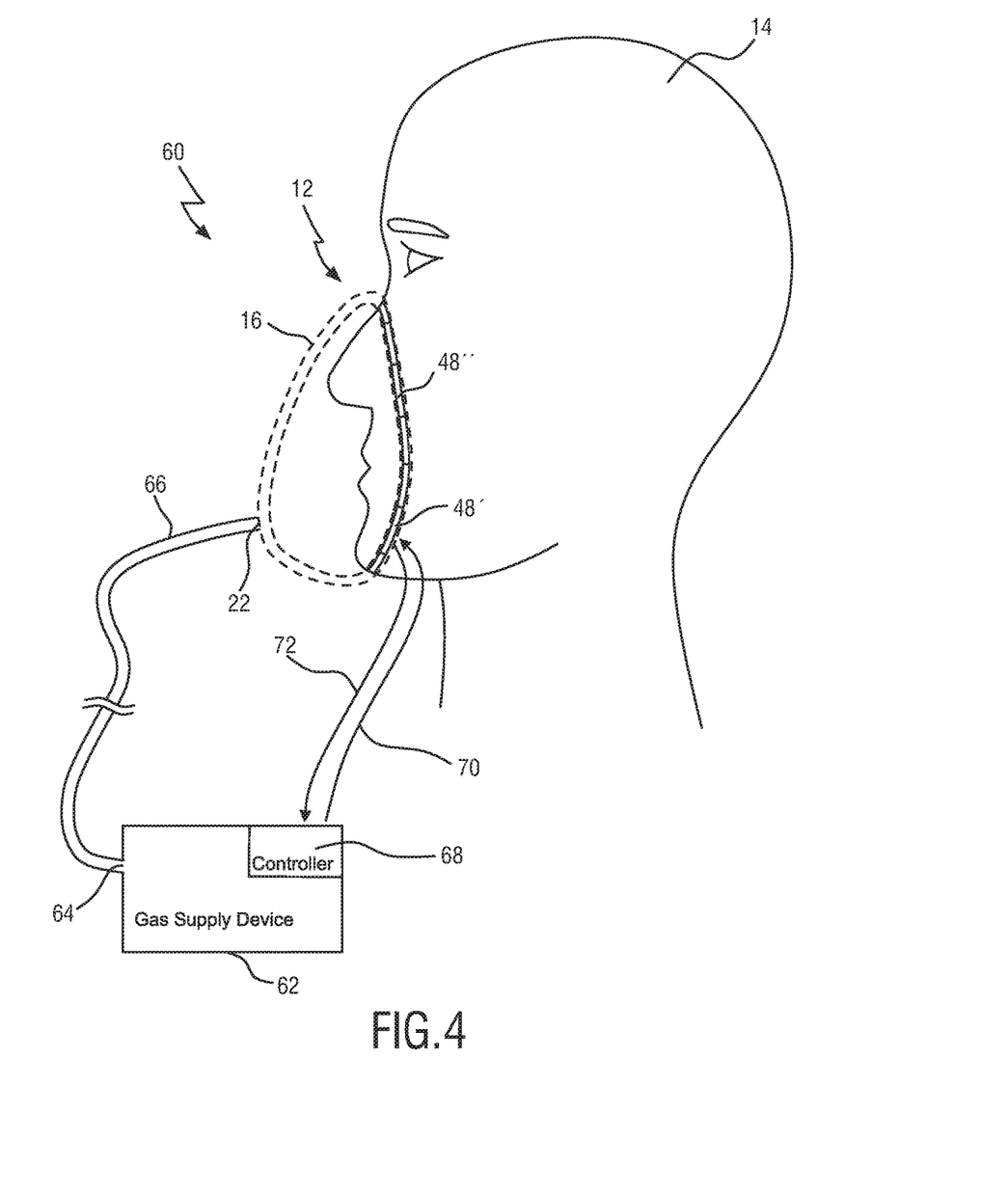
FIG. 4 shows a schematic side view of a patient wearing a patient interface according to another embodiment of the present invention and being a part of a patient interface system according to the present invention.

FIG. 4 shows the patient interface 12 as another embodiment. The patient interface 12 is in most parts identical to the patient interface 10. Therefore, identical parts are designated by the same reference numeral.

This patient interface 12 is part of the patient interface system 60. Aside from the patient interface 12, the patient interface system 60 comprises a gas supply device 62. This gas supply device 62 is preferably designed such that it provides pressurized air to the patient 14 via the patient interface 12. Therefore, the gas supply device 62 comprises a gas outlet 64, which is connected to the connector 22 of the full face mask 16 via a hose 66.

In contrast to the patient interface 10 of FIGS. 1 and 3, the patient interface 12 does not comprise a controller itself. However, in the design of the patient interface system 60, the gas supply device 62 comprises a controller 68. This controller 68 comprises the same features as already discussed within the context of the controller 50 of the embodiment of the patient interface 10. Wherein the controller 50 is arranged within the full face mask 16 of the patient interface 10, and therefore the wiring of the controller 50 with the sections 48 is relatively compact, the patient interface 12 has the benefits that due to the absence of the controller in the full face mask 16, i.e. the controller 68 being included within the gas supply device 62, the full face mask 16 of the patient interface 12 is more lightweight.

That this controller 68 is able to control the sections 48 in the patient interface 12 is exemplary illustrated with the aid of an arrow 70. This arrow 70 represents by way of example the signal or electric energy transmitted from the controller 68 to the section 48'. This control and the resulting actuation works in the same manner as described before within the context of the patient interface 10. However, in the present embodiment of the patient interface 12 the controller 68 is further designed to receive a signal, i.e. electric energy, from the sections 48, like the section 48' in this example. This electric energy, as indicated by an arrow 72, is the result of a force acting on the section 48'. This force is in this embodiment the results of the patient interface 12 pressing against the skin of the patient 14. This force normally results from a headgear of the patient interface 12, which is not shown in FIG. 4 for clarity reasons.

In the same way as the amount of electric energy 70 influences the degree of the change of the shape of the section 48', the degree of the force acting on the section 48' gives a signal/an electric energy 72 of corresponding magnitude. Accordingly, this electric energy 72 can be used by the controller 68 to analyze the force acting in the area of the section 48'. The controller 68 can then further be designed to process this data regarding the force acting in the area of the section 48' and be able to control the section 48', or any other of the sections 48, in order to reduce the pressure in the area of the section 48'. This is preferably realized by decreasing the thickness of the section 48' and, for example, by increasing the thickness of others of the sections 48 in order to alternate the shape of the cushion 18 and thereby alternating the pressure exerted on the skin of the patient 14. Although, in the example as described before it was assumed that the pressure in the area of the section 48' was too high and should therefore preferably be lowered, it is of course also possible that the controller 68 is as well designed to detect areas of lower pressure via the signals 72 received from the sections 48. Accordingly, the controller 68 would then be able to alternate the shape of the cushion 18 in a way as described before in order to increase the pressure in the aforementioned areas. This may be desirable for preventing that the fit of the patient interface 12 on the skin of the patient 14 is loosened, which may lead to a leakage of the gas, i.e. the pressurized air, transferred to the patient 14 from the gas supply device 62.

In order to determine whether the pressure of the patient interface 12 is too high or too low the controller 68 may comprise predetermined thresholds in order to compare the data received in form of the signals 72. If the threshold is passed, or the signal 72 is outside of a threshold range, the controller 68 may actuate the DEA 36 in the aforementioned manner and thereby achieve another pressure distribution, preferably such that the received signals 72 are getting back within the threshold or threshold range. The thresholds, or threshold ranges, may either be the same for every section 48 or can also be adapted to the special design of the patient interface 12, i.e. the full face mask 16 in this embodiment, and/or the individual shape of the head of the patient 14. The thresholds may also be dynamic and may change during the wearing of the patient interface 12 based on other data, like vital signs, e.g. blood pressure, pulse, or environmental data, like room temperature. Preferably they are based on the comparison of all the data received from all sections 48, that is to say that a useful evaluation whether the respective pressure is too high or too low is preferably made within the context and by comparison with the data from the other sections 48.

As mentioned before the electroactive polymer material 34, i.e. the DEA 36, may be activated either in a directed way via the controller 50 or 68 based on a given pressure situation, or in a continuous way, preferably also by one of the controllers 50 or 68, providing the patient interface 10 or 12 with a cushion 18 that changes its shape continuously over time. The latter may lead to a massaging action as mentioned before.

Without being specifically shown within the figures, the patient interfaces 10 or 12, or the patient interface system 60, may also comprise a power supply in order to actuate the electroactive polymer material 34. The power supply may be a part of the controllers 50 and/or 68. However, the controllers 50 and/or 68 may also be designed such that they are not directly transmitting electric energy to the sections 48, for example by controlling a respective separate power supply to submit the mentioned electric energy to the sections 48.

The realization of the transmittal of the signals or the electric energy from the controller 50 or 68 to the electroactive polymer materials 34, as illustrated in FIG. 4 by arrows 70 and 72, may be done in any suitable way, like combined or individual wires, a data bus-like arrangement or wireless, for example. The wiring for this may be separate or arranged on or in the hose 66, for example.

Although a specific separation of the DEA 36 into several sections 48 is shown before in the embodiments of the patient interfaces 10 and 12, it goes without mentioning that any suitable separation into several sections as desired and as preferred for an individual patient 14 lies within the scope of the present invention. Thereby, more or less sections 48 are possible. Preferred embodiments include segmented DEAs within a patient interface according to the present invention located correspondingly in the nose bridge area, the cheek area, and/or in the forehead pad.

FIG. 5 illustrates that the sections 48 of the DEA 36 can be arranged at different positions, for example, within the cushion 18 and/or 26. Due to the separated sections 48, it is possible to determine the local pressure of different regions of the patient interface 10, 12. In reaction to the pressure readings of the sections 48, the controllers 50 and/or 68 may apply an individual electrical voltage to each of the sections 48 in order to deform the cushion 18, 26 to a desired shape.

An exemplary positioning of the sections 48 within the cushions 18 and 26 of the patient interface 10', 12' is shown in FIG. 6. The reference numerals 10' and 12' are to indicate that the patient interface can be in general realized according to the embodiments shown in FIGS. 1, 3 and 4, respectively. In particular, the sections 48 can be arranged at the lateral edges of the cushions 26 and at relevant places of the cushion 18 of the full face mask 16. The locations for the sections 48 can be chosen such that the sealing quality of the cushion 18 can be reliably monitored. Consequently, the sections 48 are arranged at potential positions of the air leakages 33.

In the embodiments shown in FIG. 6 it shall be assumed that the controller 50 of the patient interface 10' as well as the controller 68 connected to the patient interface 12' are configured to read the signals 72. This allows sensing the sealing quality by evaluating the signals 72 and determining the electrical capacitances of the sections 48, since the electrical capacitances depend on the distance between the electrodes 40 and hence provide a measure for the deformation of the sections 48. Therefore, the controllers 50, 68 are enabled to detect areas of low pressure (i.e. potential spots of air leakages 33) via the signals 72 received from the sections 48. These air leakages 33, for example, can result from a shift of the patient interface 10', 12' during a change of the sleeping position of the patient 14 or from a relaxation of the facial muscles when the patient 14 falls asleep. As soon as the detected pressure falls below a predetermined threshold, the controllers 50, 68 generate the signals 70 in order to expand, extend or bend the respective sections 48 and to close the air leakages 33. This functionality allows to maintain a good sealing quality of the patient interface 10', 12' and to assure an effective medical treatment.

As a further option, the controllers 50, 68 may also be connected to an array of temperature dependent resistors (not shown), which are distributed over the cushion 18 and/or 26. The temperature dependent resistors (whose value of resistance strongly depends on the temperature) are configured to determine a temperature distribution of the cushion 18, 26. Since the air leakages 33 induce a temperature change in the cushion 18, 26 due to the missing contact to the patient's face and the flow of air, the controller 50, 68 may identify the air leakages 33 by additionally (or alternatively to the pressure readings) evaluating the temperature distribution of the cushion 18, 26. Any change in the temperature distribution can be taken as an indication for an air leakage 33.

FIG. 7 shows a schematic perspective view of the patient 14 wearing a patient interface 13 designed as a nasal mask 80. The nasal mask 80 fits over a nose 82 of the patient 14 and delivers gas to the nasal passages of the nose 82. For clarity reasons only the nasal mask 80 itself is illustrated in FIG. 7. It goes without saying that the nasal mask 80 is connected to a hose (not shown) via which the (pressurized) gas can be submitted to the patient 14. In case the nasal mask 80 is not specifically customized for the patient 14, the patient 14 feels more or less pressure on e.g. the nose 82 depending of the individual size of his/her nose 82. Consequently a large-nodes patient 14 experiences less wearing comfort due to the higher pressure which can also lead to red marks on the respective facial regions. Therefore, the inventive patient interface 13 comprises the electroactive polymer material 34, in particular, the DEA 36. As illustrated in FIG. 7, the section 48 is specifically arranged in a critical region of the nose bridge of the nose 82. The section 48 is connected either to the controller 50 or to the controller 68 according to the embodiments shown in FIGS. 3 and 4. Again, it shall be assumed that both controllers 50, 68 are configured to read the signals 72 to evaluate the pressure experienced by the patient 14 in the region of the section 48. As the controller 50, 68 receives the signals 72, it can compare the determined pressure, for example, with a predetermined pressure range defining a good wearing comfort of the nasal mask 80. If the measured pressure is out of range, the controller 50, 68 transmits the signals 70 to the section 48 in order to deform the DEA 36 and to regulate the fitting of the nasal mask 80 towards a good sealing quality and a high wearing comfort at the same time. In this way, the pressure exerted on the patient's face is independent on the size of the nose 82. Red marks e.g. on the nose bridge of large-nodes patients 14 are reduced. Time-consuming and expensive calibration work for customizing a patient interface to the individual facial geometry of a patient can be avoided.

FIG. 8 illustrates another embodiment of parts of a patient interface 110 according to the present invention. In this embodiment the cushion element 90 is ring-shaped (in fact, it has the form of a semi-complete circular tube) and the responsive material 92 (preferably electroactive polymer material) is also formed as ring. Further, an optional ring 94 of a more stiff supporting material is provided. FIG. 8A shows these parts 90, 92, 94 separately; FIG. 8B shows these parts 90, 92, 94 in the assembled state and as mounted in the patient interface. As can be seen the ring 92 of responsive material has a smaller diameter and is made thinner than the ring 90 of the cushion element (in the figure substantially the section of the cushion element is shown that touches the skin of the patient). The ring 92 of responsive material is mounted at the inner circumference of the ring 90. The ring 94 of the supporting material is arranged at the outer circumference of the ring 90.

Figure 8A:
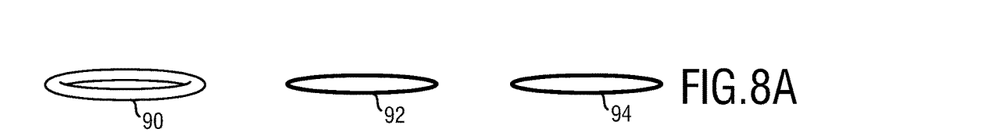
FIG. 8 illustrates another embodiment of parts of a patient interface according to the present invention.
Figure 8B:
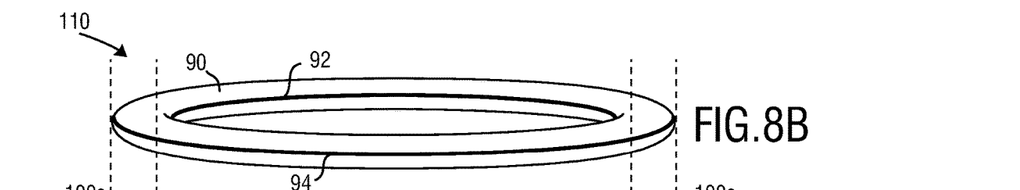
Figure 8C:
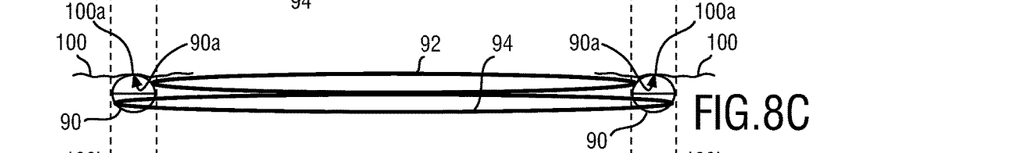
Figure 8D:
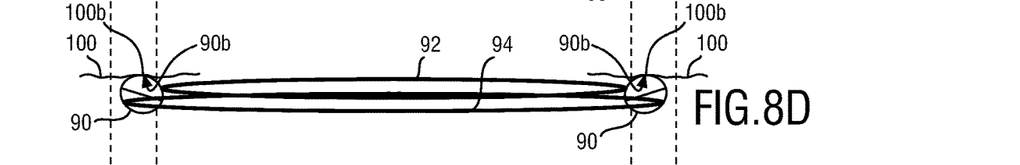

FIGS. 8C and 8D show cross-sectional views of the patient interface 110 in two different states. In the state shown in FIG. 8C the responsive material 92 is in a relaxed (non-activated) state, in the state shown in FIG. 8D the responsive material 92 is in a non-relaxed (activated) state. By the change of the state of the responsive material 92 from relaxed to activated the diameter of the ring 92 shrinks leading to a change of the position and/or size of the ring 90 which basically gets twisted by some degrees as shown in FIG. 8D compared to the position and size of the ring as shown in FIG. 8C. This has the effect that the position of contact of the ring 90 with the skin changes. In the relaxed state section 90a of the ring 90 touches section 100a of the (schematically indicated) skin 100; in the activated state section 90b of the ring 90 touches section 100b of the skin 100.

By continuously changing between these states of the responsive material 92 a positive effect for the skin can be achieved. In particular, the region of the skin that is in contact with the cushion element changes so that red marks can be reduced or avoided and moisture of the skin can dry.

FIG. 9 illustrates a cross-sectional view of parts of another embodiment of a patient interface 112 according to the present invention. In this embodiment the patient interface 112 comprises a shell 20. The cushion element 18 is mounted to the shell 20 by connectors 102, 104 of responsive material, in particular of electroactive material. In this embodiment two connectors 102, 104 of responsive material are provided, one on each side of the U-shaped ring of the cushion element 18. By alternatingly activating the connectors 102, 104 to change their size or position the position and orientation of the cushion element 18 can be changed.

Figure 9A:
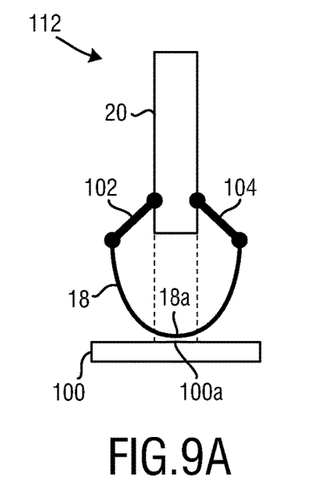
FIG. 9 illustrates still another embodiment of parts of a patient interface according to the present invention.
Figure 9B:
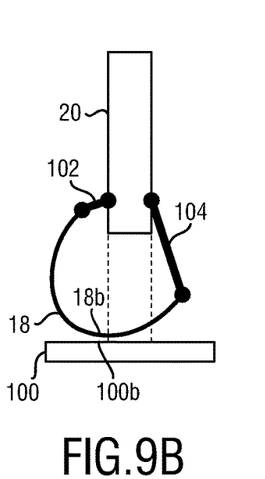
Figure 9C:
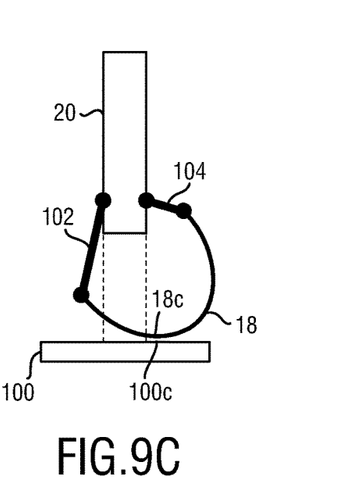

FIG. 9A shows the non-activated state of the connectors 102, 104 in which skin area 100a is in contact with section 18a of the cushion element 18. FIG. 9B shows an activated state of the connector 102, in which skin area 100b is in contact with section 18b of the cushion element 18. FIG. 9C shows an activated state of the connector 104, in which skin area 100c is in contact with section 18c of the cushion element 18.

Figure 10A:
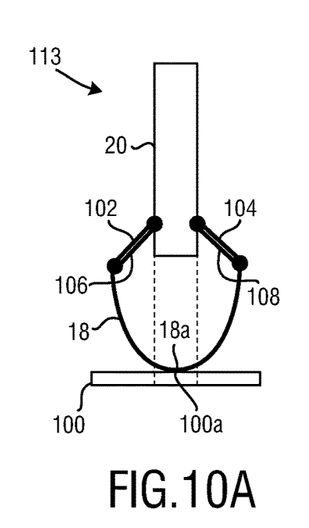
FIG. 10 illustrates still another embodiment of parts of a patient interface according to the present invention.
Figure 10B:
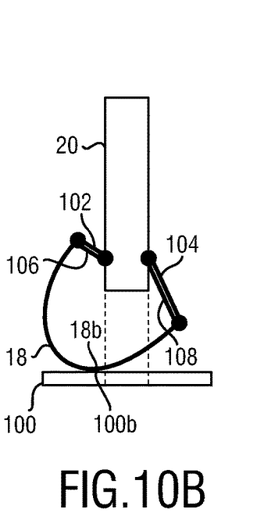
Figure 10C:
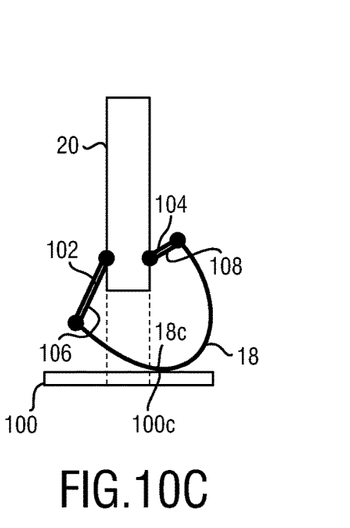

FIG. 10 illustrates a cross-sectional view of parts of still another embodiment of a patient interface 113 according to the present invention, which is based on the embodiment of the patient interface 112 shown in FIG. 9. In this embodiment the patient interface 113 comprises a support material 106, 108 arranged between the cushion element 18 and the shell 20 in parallel to the responsive material 102, 104. In particular, as shown in FIG. 10, the support material is configured in form of connectors 106, 108 similar to the connectors 102, 104 and are made of a stiff material providing mechanical support, but being able to be compressed when the parallel connector 102, 104 is activated (and, thus, compressed). Thus, a more precise mechanical movement of the cushion element can be achieved. FIGS. 10A-10C show the same states of activation of the connectors 102, 104 as shown in FIGS. 9A-9C and thus lead to basically the same movement of the cushion element 18.

The embodiments shown in FIGS. 9 and 10 thus substantially provide the same technical effects as the embodiment shown in FIG. 8, in particular enable a reduction of red marks and a drying of skin portions when the connectors 102, 104 are alternately activated when the patient interface is worn by the patient. Further, with the embodiments shown in FIGS. 8 to 10 the responsive material is not in the face-contacting part of a patient interface, in particular not in the cushion element, but the responsive material are in a non-contacting part of the patient interface. Further, the responsive material actuates in a direction having at least a component parallel to the plane of a patient's face.

The above mentioned responsive materials are not to be understood in a limiting way, i.e. other responsive materials may well be used in a patient interface according to the present invention. For instance, photo-embossing can also be used to generate surface relief structures in cross-linked polymeric gels. For instance, photo-embossing can be used to create a pattern of crosslink density in mixtures poly(N-isopropylacrylamide) and a cross-linker (ethylene glycol diacrylate). Soft gels can be produced by swelling in an aqueous environment. These structured gels exhibit an autonomous, reversible response to, for instance, temperature due to an LCST (Lower Critical Solution Temperature) transition and can thus be used as responsive material in a patient interface according to the present invention.

Further, responsive micro-structured gels may be used. The temperature and humidity response of the above-described gels can be configured by tuning the LCST transition and the corresponding transition from smooth to micro-structured surface. External triggers to switch the responsive hydro-gels such as (LED-) light can be used, for instance, by incorporating azobenzenes in the gels.

Even though the present invention is described in the context of the patient interfaces 10 and 12 comprising the full face mask 16 and the patient interface 13 comprising the nasal mask 80, it goes without mentioning that a cushion comprising a responsive material according to the present invention may be used with any of the patient interfaces mentioned before. Also, a cushion element itself that can be used with a patient interface and comprises such an electroactive polymer material or a temperature-responsive polymer material according to the present invention shall be regarded as an individual part of the present invention. Although the patient interfaces have been described on the basis of a cushion comprising an electroactive polymer material, it is to be mentioned that the patient interfaces can also be realized by using a temperature-responsive polymer material, like e.g. PNIPA, as the responsive material comprised in the cushion element.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A patient interface for delivering gas to a patient, with a cushion element that is adapted to contact the patient when the patient interface is worn by the patient, and a responsive material that is adapted to alternate at least one of: the pressure exerted by the cushion element on the patient or the area on the patient where the pressure is exerted by the cushion element, in response to a physical quantity acting on the responsive material when the patient interface is worn by the patient, wherein the cushion element comprises or is mounted to the responsive material, wherein the responsive material is an electroactive polymer material, wherein the electroactive polymer material is segmented into a plurality of segments, and wherein each segment is structured to individually receive a voltage applied thereto by a controller.

2. The patient interface of claim 1, wherein the patient interface comprises at least one dielectric elastomer actuator as the electroactive polymer material.

3. The patient interface of claim 2, wherein at least one of the dielectric elastomer actuators is prestrained.

4. The patient interface of claim 1, further comprising a shell, wherein the cushion element is mounted to the shell by the responsive material.

5. The patient interface of claim 1, wherein said cushion element is ring-shaped having an inner circumference, and wherein said responsive material is formed as a ring arranged at the inner circumference of said cushion element.

6. The patient interface of claim 1, wherein the physical quantity is one of: an electrical current, an electrical voltage, or temperature.

7. A patient interface system for delivering gas to a patient, the patient interface system comprising:
a patient interface comprising:
a cushion element that is adapted to contact the patient when the patient interface is worn by the patient, and
an electroactive polymer material that is adapted to alternate at least one of: the pressure exerted by the cushion element on the patient or the area on the patient where the pressure is exerted by the cushion element, in response to an electrical quantity acting on the electroactive polymer material when the patient interface is worn by the patient, wherein the cushion element comprises or is mounted to the electroactive polymer material;
a device for supplying gas to the patient interface; and
a controller for controlling the electroactive polymer material, wherein the controller is either comprised in the patient interface or in the device for supplying gas,
wherein the electroactive polymer material is segmented into a plurality of segments and wherein said controller is configured to one or both of: individually apply voltages to said segments and individually read voltages or capacitances from said segments.

8. The patient interface system of claim 7, wherein said controller is configured to individually read voltages or capacitances from said segments and to detect air leaks or excessive pressures between the patient interface and the patient's face from said read voltages or capacitances and to individually apply voltages to said segments at which air leaks or excessive pressures have been detected to close said air leaks or reduce said excessive pressures.

* * * * *